United States Patent [19]

Bruns et al.

[11] Patent Number: 5,002,929

[45] Date of Patent: Mar. 26, 1991

[54] DERIVATIVES OF TRIMETHYLBICYCLO-[4.3.0]-NONANE, USEFUL AS PERFUMES

[75] Inventors: Klaus Bruns, Krefeld-Traar; Thomas Gerke, Neuss; Ursula Schmitz, Krefeld-Traar, all of Fed. Rep. of Germany

[73] Assignee: Henkel Kommadnitgesellschaft auf Aktien, Duesseldorf, Fed. Rep. of Germany

[21] Appl. No.: 420,210

[22] Filed: Oct. 12, 1989

[30] Foreign Application Priority Data

Oct. 15, 1988 [DE] Fed. Rep. of Germany ....... 3835190

[51] Int. Cl.$^5$ ............................................. A61K 7/46
[52] U.S. Cl. ..................................... 512/18; 568/374; 252/174.11
[58] Field of Search ................... 568/374; 512/17, 18; 252/174.11

[56] References Cited

U.S. PATENT DOCUMENTS

| | | | |
|---|---|---|---|
| 2,933,506 | 4/1960 | Ohloff | 568/374 |
| 3,681,464 | 8/1972 | Theimer | 512/18 |
| 3,847,993 | 11/1974 | Hall et al. | 568/374 |
| 4,206,089 | 6/1980 | Willis et al. | 568/374 |
| 4,302,363 | 11/1981 | Bruns et al. | 252/522 |
| 4,555,359 | 11/1985 | Bruns et al. | 252/522 |
| 4,617,146 | 10/1986 | Helmlinger et al. | 568/374 |

OTHER PUBLICATIONS

Houben–Weyl, Methoden der Organischen Chemie, 4th Edition, vol. 4/1c, pp. 145–149 (Thieme Verlag, S. 1980).

Houben–Weyl, pp. 18–28, F. Zymalkowski: Katalytische Hydrierung.

*Primary Examiner*—James H. Reamer
*Attorney, Agent, or Firm*—Ernest G. Szoke; Wayne C. Jaeschke; Norvell E. Widsom, Jr.

[57] ABSTRACT

Certain trimethylbicylo-[4.3.0]-nonane derivatives, particularly those having a single acetyl substituent on the six membered ring, are novel compounds useful as perfumes to give highly persistent iris butter, methyl ionone, tobacco, and wood odor notes.

8 Claims, No Drawings

DERIVATIVES OF TRIMETHYLBICYCLO-[4.3.0]-NONANE, USEFUL AS PERFUMES

Field of the Invention

This invention relates to isomeric trimethylbicyclo-[4.3.0]-nonane derivatives, to a process for their preparation and to their use as perfumes.

STATEMENT OF RELATED ART

It is known from DE-OS 29 25 622 and 32 12 326 that perfumes can be made with aroma chemicals that are isomeric trimethylbicyclo-[4.3.0]-non-1-ene derivatives corresponding to general formula I:

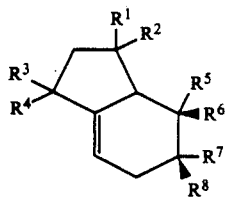

in which (i) three of the symbols $R^1$ to $R^4$ represent methyl groups and one represents a hydrogen atom and (ii) at least two of the symbols $R^5$ to $R^8$ represent hydrogen atoms; one represents CHO, $COCH_3$ or $COCH_2CH_3$; and one represents H, $CH_3$, or $CH_2CH_3$.

DESCRIPTION OF THE INVENTION

Except in the examples, all numbers in this description that specify amounts of materials or conditions of reaction or use are to be understood as modified by the term "about".

It has now been found that certain trimethylbicyclo-[4.3.0]-nonane derivatives have surprising and valuable perfume properties.

Specifically, the present invention includes a composition of matter having a chemical formula corresponding to formula II:

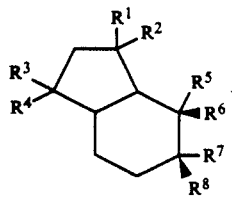

in which (i) three of the symbols $R^1$ to $R^4$ represent methyl groups and one represents a hydrogen atom and (ii) at least two of the symbols $R^5$ to $R^8$ represent hydrogen atoms; one represents CHO, $COCH_3$, or $COCH_2CH_3$; and one represents H, $CH_3$, or $CH_2CH_3$.

The present invention also relates to the use of these isomeric trimethylbicyclo-[4.3.0]-nonane derivatives as perfumes.

Preferred isomeric trimethylbicyclo-[4.3.0]-nonane derivatives corresponding to general formula II are those in which three of the substituents $R^5$ to $R^8$ represent hydrogen atoms and one represents $COCH_3$.

The bicyclo-[4.3.0]-nonanes according to the invention may be prepared in a known manner by catalytic hydrogenation of corresponding bicyclo-[4.3.0]-non-1-enes with general formula I; cf. Houben-Weyl, *Methoden der organischen Chemie*, 4th Edition, Vol. 4/1 c, pages 145–149 (Thieme Verlag, Stuttgart, 1980). Suitable catalysts are, for example, noble metals, such as palladium and/or platinum, on supports, such as barium sulfate, carbon, or aluminum oxide; nickel- and/or copper-containing catalysts, such as Raney nickel and/or Raney copper (cf. Houben-Weyl, op. cit., pp. 18–28). The hydrogenations may be carried out in bulk or in organic solvents, for example ethanol and/or cyclohexane, at temperatures in the range from 20° to 250° C. and under hydrogen pressures of from $10^5$ to $25 \cdot 10^6$ Pa. After the uptake of hydrogen has stopped, the catalyst is filtered off, the solvent is optionally distilled off and the bicyclononane-containing residue is optionally distilled under reduced pressure.

The isomeric trimethylbicyclo-[4.3.0]-non-1-enes corresponding to general formula I used as starting materials for the preparation of the trimethylbicyclo-[4.3.0]-nonanes according to the invention may be obtained by the processes described in DE-OS 29 25 622 and 32 12 326. The starting material used is a mixture of 2,2,4- and 2,4,4-trimethyl cyclopentanone in the form of an isomer mixture. Trimethyl cyclopentanone is reacted with vinyl magnesium bromide in a Grignard reaction, followed by dehydration with p-toluene sulfonic acid to 1-vinyl-2,2,4(2,4,4)-trimethyl cyclopent-1-ene. The diene mixture obtained is then converted into the isomeric trimethylbicyclo-[4.3.0]-non-1-ene derivatives corresponding to general formula I by Diels-Alder reaction with an equimolar quantity or with a slight excess of dienophilic aldehydes or ketones at temperatures in the range from 0° to 200° C. and under pressures of from $10^5$ to $2 \cdot 10^7$ pascals ("Pa"). The dienophilic aldehydes or ketones used may include acrolein, crotonaldehyde, ethyl acrolein, methyl vinyl ketone, ethyl vinyl ketone, pent-3-en-2-one, or methyl isopropenyl ketone, with methyl vinyl ketone preferred for this invention.

The compounds or isomer mixtures according to the invention have a complex odor profile dominated by iris butter, methyl ionone, tobacco, and wood notes and are distinguished by the extremely high persistence of their odor.

The bicyclononane derivatives according to the invention are suitable for the production of new and interesting perfume compositions. Based on the composition as a whole, the content of the perfume mixtures according to the invention is between 1 and 50% by weight and preferably between 1 and 25% by weight. These compositions may be used to perfume consumer goods, such as cleaning preparations and disinfectants; textile treatment preparations; cosmetics and toiletries of all kinds, such as perfumes, creams, lotions, aerosols, toilet soaps, makeup, and lipstick; and in fine fragrances. The content of the perfume compositions in the perfumed products is usually and preferably between 2 and 20% by weight.

The practice of the invention may be further appreciated from the following non-limiting examples.

EXAMPLES

1. Preparation of isomeric acetyl trimethylbicyclo-4.3.0]-nonane

One mole (206.3 g) of a mixture of 4-acetyl-7,7,9-trimethylbicyclo-[4.3.0]-non-1-ene and 5-acetyl-7,9,9-trimethylbicyclo-[4.3.0]-non-1-ene in a ratio by weight of 1:1 was dissolved in 500 milliliters ("ml") of ethanol and the resulting solution stirred with 8 grams ("g") of palladium on carbon (with a palladium content 5% by weight) for 6 hours at 22° C. under a pressure of $3 \times 10^6$ Pa of $H_2$. After the uptake of hydrogen had stopped, the catalyst was filtered off, the solvent was distilled off, and the product was distilled between 58° and 72° C. at a pressure of 13 Pa. The yield was 161 g (78% of the theoretical) of a product with the following characteristics:

Infrared absorption maxima (measured on a film of the product at the following wave numbers: 1710/cm (carbonyl), 1150/cm ($COCH_3$), 1340–1380/cm (geminal dimethyl, $COCH_3$).

Mass spectroscopy showed the major peak at the value for the molecule ion (208.3 m/e).

Proton nuclear magnetic resonance spectra (on produce dissolved in $CDCl_1$) showed nine hydrogen atoms per molecule with chemical shifts of 0.75–1.10 ppm, 3 hydrogen atoms per molecule with chemical shifts of 2.15 ppm, both the preceding being multiplet signals, and no olefinic protons detectable.

Ordor: iris butter, methyl ionone, tobacco, wood note.

Use Example

Base for men's cologne
(The abbreviation pbw stands for parts by weight.)

| | |
|---|---|
| Boisambrene forte ® | 300 pbw |
| Isomeric acetyl trimethylbicyclo-[4.3.0]-nonane from Example 1 | 100 pbw |
| Linalyl acetate | 80 pbw |
| α-Hexyl cinnamaldehyde | 80 pbw |
| Lyral ® | 60 pbw |
| Terpinyl acetate | 50 pbw |
| Patchouli oil | 50 pbw |
| Galaxolide ® | 50 pbw |
| Coumarin | 40 pbw |
| Cyclohexyl salicylate (Henkel) | 40 pbw |
| Muscatel sage oil | 30 pbw |
| Benzyl acetate | 30 pbw |
| Dodecanol, 10% by weight in dipropylene glycol | 30 pbw |
| Lemon oil | 20 pbw |
| Vetiveryl acetate | 20 pbw |
| Geranium oil Bourbon | 10 pbw |
| Rose oxide (10% by weight in dipropylene glycol) | 10 pbw |
| Total | 1000 pbw |

In the above table of ingredients for Example 2, Boisambrene forte ® is a product of Henkel KGaA, Düsseldorf; its principal constituent is ethoxymethyl cyclododecyl ether. Lyral ® and Galaxolide ® are both products of International Flavors and Fragrances and are reported by the seller to be predominantly 4-(4-hydroxy-4-methyl-pentyl)-3-cyclohexene-1-carboxaldehyde and 1,3,4,6,7,8-hexahydro-4,6,6,7,8,8-hexamethyl-cyclopenta-gamma-2-benzopyrane respectively.

What is claimed is:

1. A composition of matter corresponding to general chemical formula II:

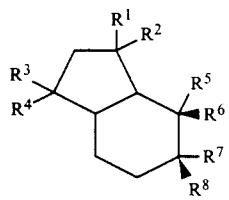

in which (i) three of the symbols $R^1$ to $R^4$ represent methyl groups and one represents a hydrogen atom and (ii) at least two of the symbols $R^5$ to $R^8$ represent hydrogen atoms; one represents CHO, $COCH_3$, or $COCH_2CH_3$; and one represents H, $CH_3$, or $CH_2CH_3$.

2. A composition according to claim 1, wherein three of the symbols $R^5$ to $R^8$ represent hydrogen atoms and one represents $COCH_3$.

3. A perfume mixture comprising a composition according to claim 2.

4. A perfume mixture comprising a composition according to claim 1.

5. A perfume mixture according to claim 4, comprising about 1 to about 50 percent by weight of a composition according to claim 1.

6. A perfume mixture according to claim 3, comprising about 1 to about 50 percent by weight of a composition according to claim 2.

7. A cleaning preparation, textile treatment preparation, cosmetic, or toiletry comprising a composition according to claim 2 as a perfume constituent.

8. A cleaning preparation, textile treatment preparation, cosmetic, or toiletry comprising a composition according to claim 1 as a perfume constituent.

* * * * *